United States Patent
Hufford

(10) Patent No.: US 11,457,985 B2
(45) Date of Patent: Oct. 4, 2022

(54) METHOD AND APPARATUS FOR ORGAN MANIPULATION USING A SURGICAL ROBOTIC SYSTEM

(71) Applicant: Asensus Surgical US, Inc., Durham, NC (US)

(72) Inventor: Kevin Andrew Hufford, Cary, NC (US)

(73) Assignee: Asensus Surgical US, Inc., Durham, NC (US)

(*) Notice: Subject to any disclaimer, the term of this patent is extended or adjusted under 35 U.S.C. 154(b) by 0 days.

(21) Appl. No.: 16/051,461

(22) Filed: Jul. 31, 2018

(65) Prior Publication Data
US 2021/0369367 A1    Dec. 2, 2021

Related U.S. Application Data

(60) Provisional application No. 62/539,524, filed on Jul. 31, 2017.

(51) Int. Cl.
| | |
|---|---|
| *A61B 34/37* | (2016.01) |
| *A61B 90/50* | (2016.01) |
| *A61B 34/00* | (2016.01) |
| *A61B 34/30* | (2016.01) |

(52) U.S. Cl.
CPC ............. *A61B 34/37* (2016.02); *A61B 34/74* (2016.02); *A61B 90/50* (2016.02); *A61B 2034/302* (2016.02)

(58) Field of Classification Search
CPC ......... A61B 34/37; A61B 34/74; A61B 90/50; A61B 2034/302
See application file for complete search history.

(56) References Cited

U.S. PATENT DOCUMENTS

| | | | |
|---|---|---|---|
| 2006/0235436 A1* | 10/2006 | Anderson | A61B 34/30 606/130 |
| 2008/0221590 A1 | 9/2008 | Ikeda et al. | |
| 2010/0331859 A1* | 12/2010 | Omori | A61B 34/71 606/130 |
| 2011/0152615 A1* | 6/2011 | Schostek | A61B 34/30 600/111 |

FOREIGN PATENT DOCUMENTS

WO    2016059445 A1    4/2016

OTHER PUBLICATIONS

Akrivos et al., "A pilot study of robotic uterine and vaginal vault manipulation: The ViKY Uterine Positioner" Journal of Robotic Surgery (Apr. 2013).

* cited by examiner

*Primary Examiner* — Richard G Louis

(57) ABSTRACT

In a robotic surgical system, an organ manipulation device such as a uterine manipulator with a colpotomy cup is positionable on a first robotic manipulator while a surgical instrument is positionable on a second robotic manipulator. During the course of surgery, a user inputs instructions to the robotic surgical system to cause movement of the organ manipulator and surgical instrument.

9 Claims, 3 Drawing Sheets

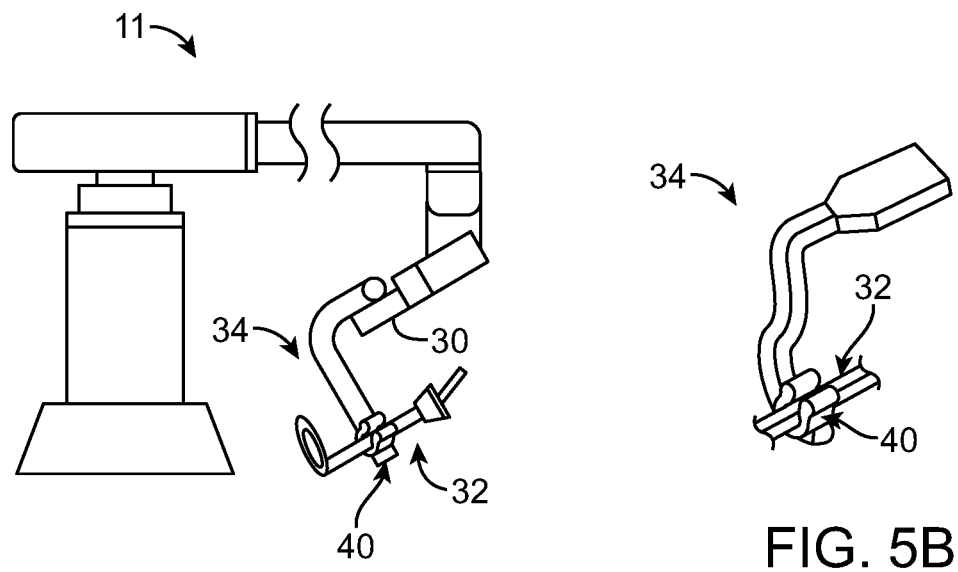
FIG. 5A
FIG. 5B
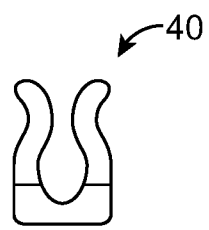
FIG. 5C

METHOD AND APPARATUS FOR ORGAN MANIPULATION USING A SURGICAL ROBOTIC SYSTEM

This application claims the benefit of U.S. Provisional Application 62/539,524, filed Jul. 31, 2017.

TECHNICAL FIELD OF THE INVENTION

The present invention relates generally to the field of surgical robotic systems.

BACKGROUND

Current surgical robotic systems utilize robotic manipulator arms that support and maneuver surgical instruments.

During surgery, it might be necessary for surgical staff to manipulate certain organs to move them away from the field of interest or to place them in a position and/or orientation that facilitates work that is to be done on them.

During a hysterectomy, it is necessary to cut the vaginal cuff circumferentially to detach the uterus from the vagina. To accomplish both an anterior colpotomy and posterior colpotomy, it is necessary to move the uterus up/down, left/right for access, as well as axially to provide adequate tissue tension at the cuff.

A uterine manipulator is often held by a surgical assistant and manually manipulated to provide the necessary motions and tissue tension. Some examples of commercial devices for uterine manipulation are shown in FIGS. 2 and 3. Both are shown with colpotomy cups attached, which, in use for laparoscopic hysterectomy are positioned in engagement with the external os of the cervix and provide a rigid circular surface against which to cut, but these are not necessarily required to perform a colpotomy.

The manual manipulation often leads to fatigue for the assistant, and often requires communication from the surgeon to direct the motion. To provide more rigid uterine manipulation, some have made uterine manipulation devices. One such device is shown in FIG. 4. It includes a segmented arm that holds a uterine manipulator. This segmented arm is able to become compliant with the press of a foot pedal. Upon releasing the foot pedal, it becomes rigid and holds a given position.

US Published Application No. 2013/0030571 (the '571 application), which is owned by the owner of the present application and which is incorporated herein by reference, describes a robotic surgical system that includes an eye tracking system. The eye tracking system detects the direction of the surgeon's gaze and enters commands to the surgical system based on the detected direction of the gaze.

FIG. 1 is a schematic view of the prior art robotic surgery system 10 of the '571. The system 10 comprises at least one robotic arm which acts under the control of a control console 12 managed by the surgeon who may be seated at the console. The system shown in FIG. 1 includes multiple robotic arms 11a, 11b, 11c. Three such arms are shown but a larger or smaller number may be used. Each robotic arm can support and operate a surgical instrument 9a, 9b, 9c for use on a patient 13. One of the instruments is preferably a camera which records the operating field inside the patient, while the other instruments may be known surgical tools 15, 16.

The arms 11a, 11b, 11c are operated by an electronic control unit 30 which causes the arms to perform the movements entered via the console 12. The unit 30 will receive the high-level movement commands (for example, desired position and inclination of the tool supported by the robot) and will execute them, converting them into the corresponding sequences of signals to be sent to the individual motors of the robot arm articulations. Other details of the system 10 are found in the '571 application which is fully incorporated herein by reference.

The console includes input devices 17, 18 which can be gripped by the surgeon and moved so as to deliver instructions to the system as to the desired movement and operation of the instruments supported by the arms 11a, 11b, 11c.

The surgeon's movements are suitably reproduced by the surgical instruments by means of movement of the robotic arms. The input devices may be equipped to provide the surgeon with tactile feedback so that the surgeon can feel on the input devices 17, 18 the forces exerted by the instruments on the patient's tissues.

Each input device will typically operate a robot arm. The '571 application describes that where there are two input handles and more than two arms carrying instruments, the system includes a control on the console that allows the surgeon to assign each arm to a desired instrument. This allows a surgeon to control of two of the surgical instruments disposed at the working site at any given time. To control a third instrument disposed at the working site, one of the two handles 17, 18 is operatively disengaged from one of the initial two instruments and then operatively paired with the third instrument.

The console may also include a keyboard 19 and/or touch screen and/or other command input devices. These other command devices might include a pedal device 20, and a button(s) on or in proximity to one or both handles of the input devices 17, 18.

The console 12 has an eye movement tracking system 21 or so-called "eye tracker" for detecting the direction of the surgeon's gaze towards the console and for controlling the surgical system depending on the gaze directions detected. In this way, the surgeon may control functions of the system by means of movement of his/her eyes.

The tracking system estimates the direction of the surgeon's gaze towards the display 22 and performs selection of the commands associated with a zone when it detects a gaze direction which falls within this zone. In one particular example, the commands associated with selection areas 29 on the display 22 comprise the commands for assigning particular ones of the arms to the surgeon input devices. That allows the surgeon to alternate control of the robot arms on the two input devices without letting go of the input devices, but instead by simply looking at the corresponding selection areas on the screen. For example, while controlling each of the arms 11a, 11c with one of the input devices 17, 18, the user might re-assign input device 17 over to arm 11b in order to use or reposition the instrument 9b within the body. Once the task involving movement of instrument 9b is completed, the surgeon can rapidly re-assign input device 17 back to robot arm 11a. These steps can be performed by using the eye tracking features to "drag and drop" icons on the console display towards icons representing the various arms.

In another example described in the '571, the eye tracking system is used to move the camera based on where the surgeon is looking on the display 22. When this function is enabled (e.g. by entering an input command, such as through pressing of a button on the console, depressing a foot pedal, etc.), the movement of the eyes over the image of the operating field on the screen causes the movement of the robot arm supporting the camera. This can be used to place the zone the surgeon focused on at the center of the display screen.

The '571 also describes use of the eye tracker to detect the distance between the screen and surgeon's eyes as a way to allow the surgeon to "zoom" the camera display in or out. The system enlarges the picture of the operating field shown on the screen depending on a variation in the distance detected. With this feature, the surgeon can intuitively perform enlargement of the picture by simply moving his/her face towards the screen and, vice versa, increase the viewing area of the operating field, thus reducing enlargement, by moving his/her face away from the screen.

The present application describes a system and method allowing control of an organ or tissue manipulation device such as a uterine manipulator during robotic surgical procedures.

BRIEF DESCRIPTION OF THE DRAWINGS

FIGS. 5A-5C show an exemplary system using a uterine manipulator on a robotic surgical system.

DETAILED DESCRIPTION

The invention comprises an apparatus and method for manipulating a uterus or other organ with a surgical robotic system. A surgical system employing the concepts described here includes one or more robotic arms, and surgical instruments mountable to and moveable by the arms in response to input from a user input device. The system includes features allowing attachment of an organ manipulator such a uterine manipulator to one of the robotic arms. The uterine manipulator may be an existing commercially-available device, such as a RUMI, V-Care Cup, a uterine sound, or an alternate device that can engage and move or reposition a uterus or other body organ within the body.

Figure 1:
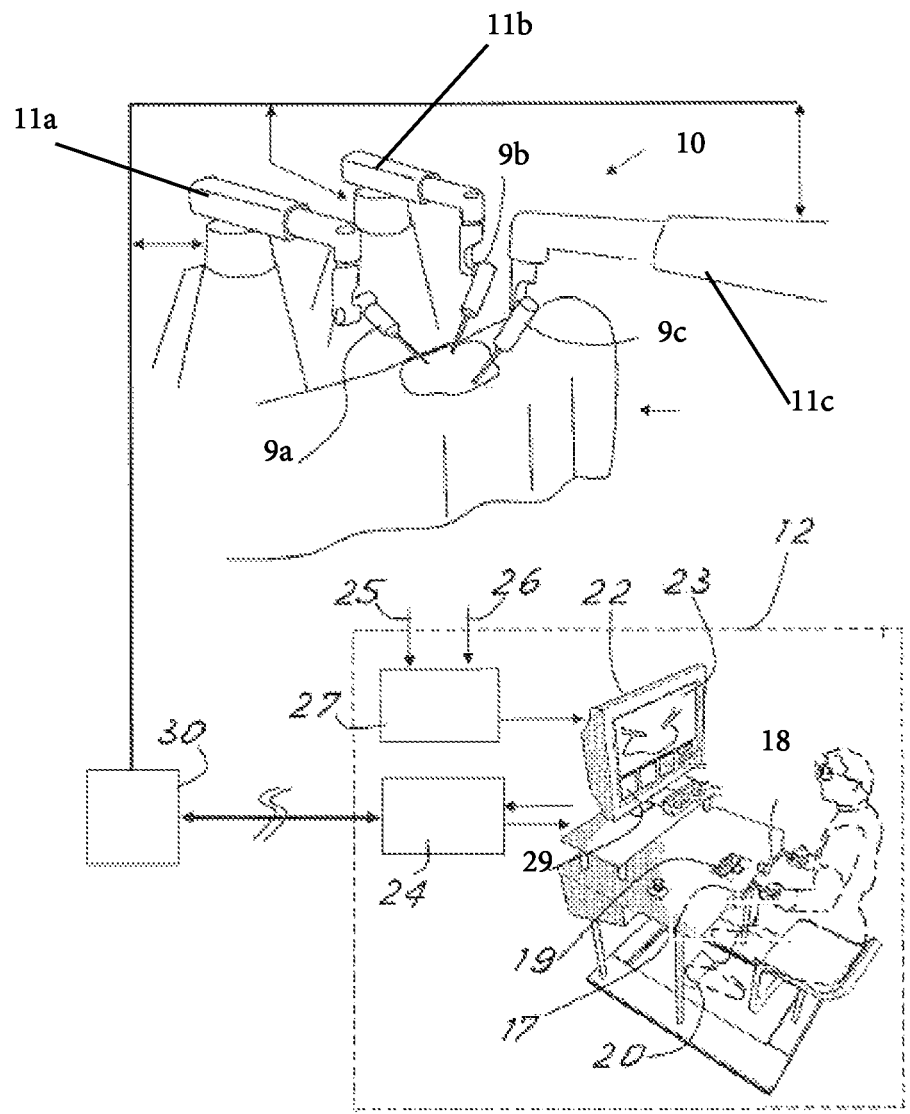
FIG. 1 is a schematic view of a robotic surgery system.
Figure 2:
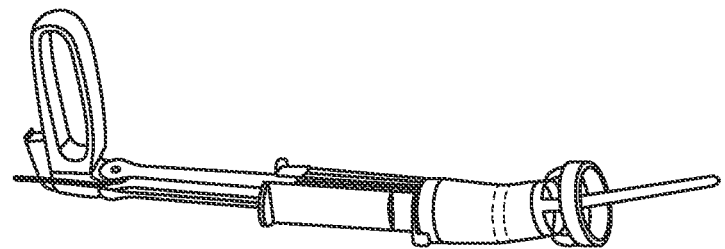
FIGS. 2 and 3 show uterine manipulators of the prior art.
Figure 3:
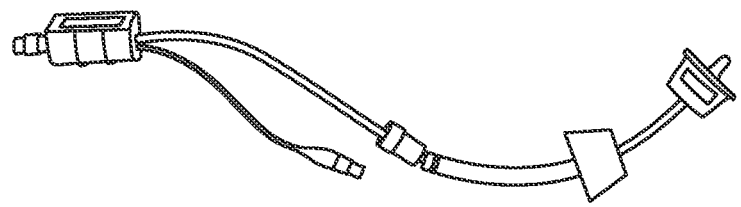
Figure 4:
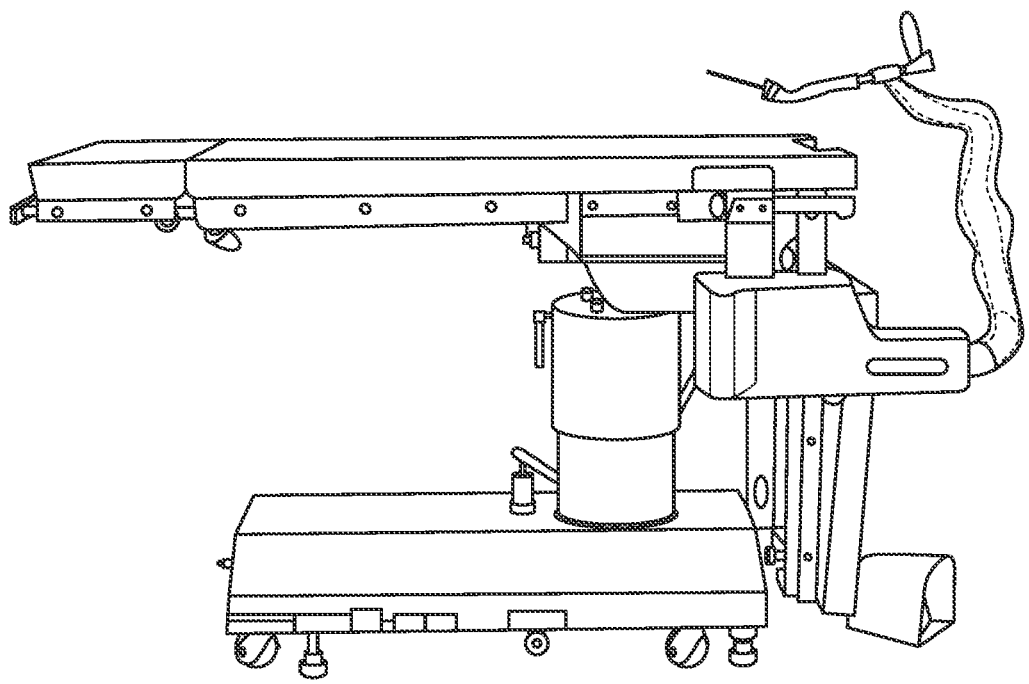
FIG. 4 shows a uterine manipulation system of the prior art.

FIG. 5A shows a robotic manipulator arm of the type shown in FIG. 1. The robotic arm 11 may be part of a robotic surgical system of the type shown in FIG. 1. The surgical system may be a multi-arm system, with one arm supporting an organ manipulator such as a uterine manipulator, at least one arm supporting another surgical instrument such a cutting instrument, electrosurgical instrument etc., and a third supporting a camera for positioning within the patient. The organ manipulator 32 is removably attachable to the end effector 30 of the robotic arm. FIG. 5B shows an intermediate member or adaptor 34 that mounts to the end effector 30 and that receives the organ manipulator 32. Adaptor 34 and manipulator 32 may be provided as sterile pieces, while the end effector 30 may be a non-sterile component covered by a sterile drape or barrier. A clip 40 (FIG. 5C), lock, interlocking feature, or other type of attachment device is used to attach the uterine manipulator to the adaptor or to the end effector where no adaptor is used. This attachment device may be a permanent part of the robotic arm or adaptor, or it may be interchangeable with other attachment devices, each allowing attachment of a different type of uterine/organ manipulator to the robotic arm or manipulator. In other implementations, the uterine manipulator and attachment may be more integrated (or may even be a single piece).

In the implementation shown in FIG. 5A, the end effector 30 of the robotic arm is positioned above the abdomen of the patient, pointed down toward the patient's legs. In another implementation, the end effector may be positioned between the patient's legs, pointed up toward the pelvic region.

The invention also comprises a method of manipulating the uterus with a robotic input. In some implementations, the surgeon is able to use laparoscopic-style motion to manipulate the uterus, almost as if it were a laparoscopic instrument. For example, using hands on the input devices 17, 18, the surgeon uses one input device 17 to control one robotic arm to control the position and/or orientation of the uterine manipulator (via the robotically moveable uterine manipulator), and the other input device 18 to control a different robotic arm to control the position, orientation and/or operation of a surgical device being used to treat the uterus or surrounding tissue. In a laparoscopic hysterectomy, therefore, the surgeon can use one hand to control manipulation of the uterus and the other hand to perform the cutting. In one configuration, the motion of the uterine manipulator is mapped to the user input device so that the robotic uterine manipulator, pointed toward the feet of the patient, moves in the manner of a laparoscopic instrument, moving relative to a fulcrum. In a second configuration, in which the robotic end effector is pointed up toward the vagina, the robot control system may perform mathematical operations/kinematics to map the motion differently to accomplish the same user experience. In some implementations, the motion may be mapped to Cartesian style motion which the user may not perceive to be moving about a fulcrum.

In some implementations, the robotic system may be able to determine a fulcrum/remote-center-of-motion that is located at an anatomical landmark, such as at the vaginal opening, in order to minimize tissue trauma, distension, or post-operative pain. This determination may be accomplished via methodologies similar to those described in US Publication No. 2010/0094312 which is attached at the Appendix and incorporated herein by reference. In other implementations, the surgeon may be able to manually set the fulcrum location.

In certain procedures, two robotic arms may be employed to move the uterus. For example, one robotic arm might be used to control an instrument placed internal to the uterus (RUMI®, uterine sound, etc.) and another robotic arm might be used to control an instrument used to grasp the exterior of the uterus (rat-tooth grasper/tenaculum, etc.). In this implementation, manipulation of a single input 17 or 18 from the surgeon may cause two of the robotic arms to move in concert. This may be simple position control and tracking, or may be enhanced with force control means to minimize potentially-traumatic forces to the body. Alternatively, the surgeon might give input for one device using the left hand control 17 and give input for the other device using the right hand control 18.

The concepts described in this application allow the surgeon to directly manipulate the uterus, rather than relying on an assistant, allowing for stable control of the uterus, and allowing the surgeon to directly coordinate movement of the uterus/organ with the other instruments being operated by the surgeon.

What is claimed is:
1. A surgical method comprising:
    positioning an organ manipulator on a first robotic manipulator arm, wherein the organ manipulator is a uterine manipulator having a culpotomy ring;
    positioning a surgical instrument on a second robotic manipulator arm, wherein the surgical instrument is a cutting instrument; and
    using user input devices, inputting instructions to the robotic surgical system to cause movement of the organ manipulator and surgical instrument in response to the instructions; and using the cutting instrument to cut around the culpotomy ring.

2. The method of claim 1, wherein the system includes a user console and the method includes inputting instructions using a first input handle of the user console to cause movement of the organ manipulator, and inputting instructions to the second input handle to cause movement of the surgical instrument.

3. The method of claim 2, where a single person operates the first and second input handles to input the instructions.

4. The method of claim 1, wherein the system includes a first input handle, the robotic surgical system configured such that the first input handle is selectively paired with a first one of the robotic arms such that input to the first input handle results in movement of the organ manipulator, and selectively paired with a second one of the robotic arms such that input to the first input handle results in movement of the surgical instrument.

5. The method of claim 1, wherein movement of the organ manipulator is laparoscopic movement relative to a fulcrum.

6. The method of claim 5, further including the steps of positioning the organ manipulator within an organ, determining a fulcrum along an axis of the organ manipulator relative to an anatomical feature, and then pivoting the organ manipulator relative to the fulcrum.

7. The method of claim 6, wherein the anatomical feature is an incision site.

8. The method of claim 6, wherein the anatomical feature is a natural orifice.

9. The method of claim 8, wherein the natural orifice is a vaginal opening.

* * * * *